US009345655B2

(12) United States Patent
Vazquez et al.

(10) Patent No.: US 9,345,655 B2
(45) Date of Patent: May 24, 2016

(54) ORAL CARE COMPOSITIONS

(75) Inventors: Joe Vazquez, Hamilton, NJ (US); Dandan Chen, Bridgewater, NJ (US); Harsh M. Trivedi, Hillsborough, NJ (US); Ammanuel Mehreteab, Piscataway, NJ (US); Laurence Du-Thumm, Princeton, NJ (US); Gregory Szewzyk, Flemington, NJ (US); Zhigang Hao, Bridgewater, NJ (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 14/364,283

(22) PCT Filed: Dec. 21, 2011

(86) PCT No.: PCT/US2011/066482
§ 371 (c)(1),
(2), (4) Date: Jul. 29, 2014

(87) PCT Pub. No.: WO2013/109236
PCT Pub. Date: Jul. 25, 2013

(65) Prior Publication Data
US 2014/0369941 A1    Dec. 18, 2014

(51) Int. Cl.
*A61K 8/63* (2006.01)
*A61Q 11/00* (2006.01)
*A61K 8/49* (2006.01)
*A61K 8/21* (2006.01)

(52) U.S. Cl.
CPC ... *A61K 8/63* (2013.01); *A61K 8/21* (2013.01); *A61K 8/4926* (2013.01); *A61Q 11/00* (2013.01)

(58) Field of Classification Search
USPC ................................... 424/49, 54
See application file for complete search history.

(56) References Cited

U.S. PATENT DOCUMENTS

| 4,661,341 A | 4/1987 | Benedict et al. |
| 4,842,593 A | 6/1989 | Jordan et al. |
| 4,865,855 A | 9/1989 | Hansen et al. |
| 4,972,848 A | 11/1990 | DiDomenico |
| 5,025,754 A | 6/1991 | Plyler |
| 5,286,479 A * | 2/1994 | Garlich et al. .................. 424/54 |
| 5,310,545 A | 5/1994 | Eisen |
| 5,356,630 A | 10/1994 | Laurencin et al. |
| 5,380,839 A | 1/1995 | McCall et al. |
| 5,552,057 A | 9/1996 | Hughes et al. |
| 5,721,359 A | 2/1998 | Dunn et al. |
| 6,117,332 A | 9/2000 | Hatch et al. |
| 6,228,393 B1 | 5/2001 | DiCosmo et al. |
| 6,350,738 B1 | 2/2002 | Savage et al. |
| 6,486,148 B2 | 11/2002 | Savage et al. |
| 6,562,318 B1 | 5/2003 | Filler |
| 6,673,771 B1 | 1/2004 | Greene et al. |
| 6,767,904 B2 | 7/2004 | Savage et al. |
| 6,803,066 B2 | 10/2004 | Traeder |
| 6,872,303 B2 | 3/2005 | Knapp et al. |
| 6,939,376 B2 | 9/2005 | Shulze et al. |
| 7,282,214 B2 | 10/2007 | Willcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 2002/0091278 A1 | 7/2002 | Savage et al. |
| 2003/0099717 A1 | 5/2003 | Cabrera |
| 2004/0009227 A1 | 1/2004 | Yao |
| 2004/0058974 A1 | 3/2004 | Courtney et al. |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0106393 A1 | 5/2007 | Miles et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0174035 A1 | 7/2008 | Winterton |
| 2008/0188819 A1 | 8/2008 | Kloke et al. |

(Continued)

FOREIGN PATENT DOCUMENTS

| CN | 101378761 | 3/2009 |
| CN | 102172356 | 9/2011 |
| EP | 0341951 | 11/1989 |
| EP | 1208844 | 5/2002 |
| JO | 2010533051 | 10/2010 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |

(Continued)

OTHER PUBLICATIONS

Isogai, E. et al. (2009). "Ceragenin CSA-13 exhibits antimicrobial activity against cariogenic and periodontopathic bacterial." Oral Microbiology and Immunology, 24(2): 170-172.*

(Continued)

*Primary Examiner* — Frederick Krass
*Assistant Examiner* — Amanda Heyes
(74) *Attorney, Agent, or Firm* — Workman Nydegger

(57) ABSTRACT

Aqueous oral compositions containing a cationic steroidal compound and a quaternary ammonium compound are suitable for treating conditions of the oral cavity.

13 Claims, No Drawing

(56) References Cited

U.S. PATENT DOCUMENTS

| | | |
|---|---|---|
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0324517 A1 | 12/2009 | Kline |
| 2010/0330086 A1 | 12/2010 | Savage et al. |
| 2011/0091376 A1 | 4/2011 | Savage |
| 2011/0123624 A1 | 5/2011 | Zasloff |
| 2012/0088733 A1 | 4/2012 | Kim et al. |
| 2012/0107382 A1 | 5/2012 | Savage et al. |
| 2013/0022651 A1 | 1/2013 | Savage |
| 2013/0053507 A1 | 2/2013 | Savage |
| 2013/0234842 A1 | 9/2013 | Genberg et al. |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0245760 A1 | 9/2013 | Savage et al. |
| 2013/0280312 A1 | 10/2013 | De Szalay |
| 2013/0280391 A1 | 10/2013 | Savage |
| 2014/0107090 A1 | 4/2014 | Beus et al. |
| 2014/0194401 A1 | 7/2014 | Genberg et al. |
| 2014/0271761 A1 | 9/2014 | Savage et al. |
| 2014/0274913 A1 | 9/2014 | Savage et al. |
| 2014/0315873 A1 | 10/2014 | Beus et al. |
| 2015/0140063 A1 | 5/2015 | Savage |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |

FOREIGN PATENT DOCUMENTS

| | | |
|---|---|---|
| JP | 2002538093 | 11/2002 |
| JP | 2004506645 | 3/2004 |
| JP | 2010538074 | 12/2010 |
| JP | 2011527702 | 11/2011 |
| JP | 2014500741 | 1/2014 |
| WO | WO 9524415 | 9/1995 |
| WO | WO 9944616 | 9/1999 |
| WO | WO 0042058 | 7/2000 |
| WO | WO 0214342 | 2/2002 |
| WO | WO02067979 | 9/2002 |
| WO | WO 03015757 | 2/2003 |
| WO | WO 03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO 2008038965 | 4/2008 |
| WO | WO 2009079066 | 6/2009 |
| WO | WO2010006192 | 1/2010 |
| WO | WO 2010036427 | 4/2010 |
| WO | WO 2010062562 | 6/2010 |
| WO | WO2011066260 | 6/2011 |
| WO | WO 2011109704 | 9/2011 |
| WO | WO 2012061651 | 5/2012 |
| WO | WO 2013029055 | 2/2013 |
| WO | WO 2013029059 | 2/2013 |
| WO | WO 2013109236 | 7/2013 |

OTHER PUBLICATIONS

U.S. Appl. No. 13/783,007, filed Mar. 1, 2013, Savage.
U.S. Appl. No. 14/288,126, filed May 27, 2014, Savage et al.
U.S. Appl. No. 14/339,342, filed Jul. 23, 2014, Vazquez et al.
U.S. Appl. No. 14/341,304, filed Jul. 25, 2014, Savage et al.
U.S. Appl. No. 14/398,094, filed Oct. 30, 2014, Savage et al.
U.S. Appl. No. 14/515,858, filed Oct. 16, 2014, Savage et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999, pp. 1865-1868, XP004155984, ISSN: 0040-4039, DOI: 10.1016/S0040-4039(99)00075-1.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000, pp. 2837-2840.
Qunying Guan et al: "Supporting Information: Preparation and Characterization of Cholic Acid-Derived Antimicrobial Agents with Controlled Stabilities", Organic Letters, Aug. 17, 2000, pp. 1-7, XP55017313, Retrieved from the Internet: URL:http://pubs.acs.org/doi/suppl/10.1021/o10062704/suppl_file/o10062704_sl.pdf.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009, pp. 170-172.
International Search Report for PCT Application No. PCT/US2009/0475485 dated Feb. 17, 2010.
International Search Report for PCT Application No. PCT/US2011/059225 dated Jan. 31, 2012.
International Search Report for PCT Application No. PCT/US2012/047750, Mailed Date: Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, Mailed Date: Jul. 24, 2013.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.

(56) References Cited

OTHER PUBLICATIONS

P. B. Savage, et al., "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld, et al., "Cow-specific treatment of clinical mastitis: an economic approach", Journal of Dairy Science vol. 94, Jan. 2011, pp. 174-188.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008, pp. 124-134.
Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
U.S. Appl. No. 13/000,010, filed Dec. 17, 2012, Restriction Requirement dated Dec. 4, 2012.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.
U.S. Appl. No. 13/288,892, Nov. 3, 2011, Notice of Allowance dated Nov. 29, 2013.
U.S. Appl. No. 13/288,902, filed Nov. 3, 2011, Restriction Requirement dated Jun. 21, 2012.
U.S. Appl. No. 13/288,902, filed Nov. 3, 2011, Office Action dated Nov. 7, 2012.
U.S. Appl. No. 13/288,902, filed Nov. 3, 2011, Notice of Allowance dated Aug. 9, 2013.
U.S. Appl. No. 13/554,930, filed Jul. 20, 2012, Office Action dated Jul. 11, 2014.
U.S. Appl. No. 13/554,957, filed Jul. 20, 2012, Office Action dated Apr. 1, 2014.
U.S. Appl. No. 13/554,957, filed Jul. 20, 2012, Notice of Allowance dated Aug. 1, 2014.
U.S. Appl. No. 13/594,608, filed Aug. 24, 2012, Office Action dated Jan. 30, 2014.
U.S. Appl. No. 13/594,612, filed Aug. 24, 2012, Office Action dated May 15, 2014.
U.S. Appl. No. 13/615,324, filed Sep. 13, 2012, Office Action dated Jan. 30, 2014.
U.S. Appl. No. 13/783,131, filed Mar. 1, 2013, Office Action dated Oct. 23, 2014.
U.S. Appl. No. 14/056,122, filed Oct. 17, 2013, Office Action dated Sep. 3, 2014.
U.S. Appl. No. 13/615,244, filed Sep. 13, 2012, Office Action dated Jan. 16, 2015.
U.S. Appl. No. 14/257,776, filed Apr. 21, 2014, Restriction Requirement dated Jan. 22, 2015.
Pitten F-A et al: "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Paul B. Savage, et al: "Antibacterial Properties of cationic steroid antibiotics", FEMS Microbiology Letters, vol. 217, 2002, pp. 1-7.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Suzuki et al., "Molecular Genetics of Plant Sterol Backbone Synthesis", 2007; Lipids; 42: 47-54.
Van Den Bogaard et al., "Antibiotic Usage in Animals: Impact on Bacterial Resistance and Public Health"; 1999; Drugs; 58 (4): 589-607.
U.S. Appl. No. 14/339,342, filed Jul. 23, 2014, Office Action dated Mar. 5, 2015.
U.S. Appl. No. 13/554,930, filed Jul. 20, 2012, Final Office Action dated Mar. 16, 2015.
U.S. Appl. No. 13/783,007, filed Mar. 1, 2013, Restriction Requirement dated Mar. 31, 2015.
U.S. Appl. No. 13/000,010, filed Dec. 17, 2010, Office Action dated Apr. 14, 2015.
U.S. Appl. No. 14/257,776, filed Apr. 21, 2014, Office Action dated Apr. 16, 2015.
U.S. Appl. No. 14/364,283, filed Jul. 29, 2014, Office Action dated Feb. 11, 2015.
U.S. Appl. No. 14/694,028, filed Apr. 23, 2015, Beus et al.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/873,013, filed Oct. 1, 2015, Savage et al.
U.S. Appl. No. 14/926,738, filed Oct. 29, 2015, Vazquez et al.
U.S. Appl. No. 14/750,928, filed Jun. 25, 2015, Genberg et al.
U.S. Appl. No. 14/875,953, filed Oct. 6, 2015, Savage.
U.S. Appl. No. 14/830,356, filed Aug. 19, 2015, Savage.
U.S. Appl. No. 14/866,213, filed Sep. 25, 2015, Savage.
Berge et al., "Pharmaceutical Salts", Journal of Pharmaceutical Sciences, Jan. 1977, vol. 66, No. 1, pp. 1-19.
Clara et al., "Preclinical evaluation of magainin-A as a contraceptive antimicrobial agent", Fertility and Sterility 81 (5), pp. 1357-1365, 20.
International Search Report for PCT Application No. PCT/US2013/065510 dated Apr. 30, 2015.
International Search Report for PCT Application No. PCT/US2014/034986 dated Aug. 28, 2014.
International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinicial trail on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Zanger et al., "Structure-Activity Relationship and Drug Design", Remington's Pharmaceutical Sciences, Chapter 27, 16th Edition, 1980, pp. 420-425.
U.S. Appl. No. 14/339,342, filed Jul. 23, 2014, Final Office Action dated Sep. 25, 2015.

* cited by examiner

ORAL CARE COMPOSITIONS

BACKGROUND

Ceragenins are cationic steroid antimicrobials that are synthetically produced from a sterol backbone.

Quaternary ammonium compounds are known to have antibacterial activity and their use in oral care is also known. However, oral care products containing a combination of a quaternary ammonium compound together with a cationic steroidal compound have heretofore been unknown.

SUMMARY

Some embodiments of the present invention provide an aqueous oral care composition comprising: a cationic steroidal compound; and a quaternary ammonium compound.

Other embodiments provide methods of treating a disease or condition of the oral cavity comprising administering a composition according to any of the foregoing claims to the oral cavity of a subject in need thereof Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Some embodiments of the present invention provide an aqueous oral care composition comprising: a cationic steroidal compound; and a quaternary ammonium compound.

As used herein, the term "aqueous" refers to a free water content of at least about 40%, by weight.

In some embodiments, the compositions comprise from about 40 to about 97%, by weight, free water. In some embodiments, the compositions comprise greater than about 50%, by weight, free water. In some embodiments, the compositions comprise from about 50 to about 90%, by weight, free water. In some embodiments, the compositions comprise from about 60 to about 85%, by weight, free water. In some embodiments, the compositions comprise from about 73% to about 83%, by weight, free water. Some embodiments comprise about 74%, about 75%, about 76%, about 77%, about 78%, about 79%, about 80%, about 81% or about 82%, by weight, free water.

In some embodiments, the cationic steroidal compound is a compound of Formula (I):

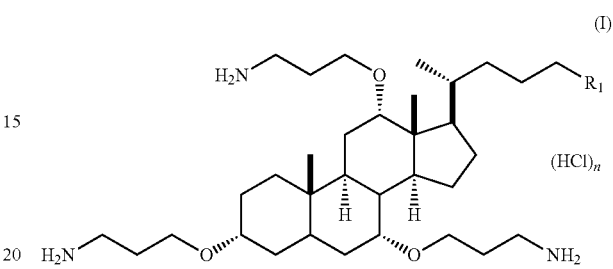

(I)

wherein $R_1$ is selected from —OH and NH—$R_2$, wherein $R_2$ is $C_2$-$C_{14}$ alkyl, $C_2$-$C_{14}$ alkenyl or $C_2$-$C_{14}$ akynyl, and n is 3 or 4.

Some embodiments provide a composition wherein the compound of Formula (I), is selected from a compound of Formula (II):

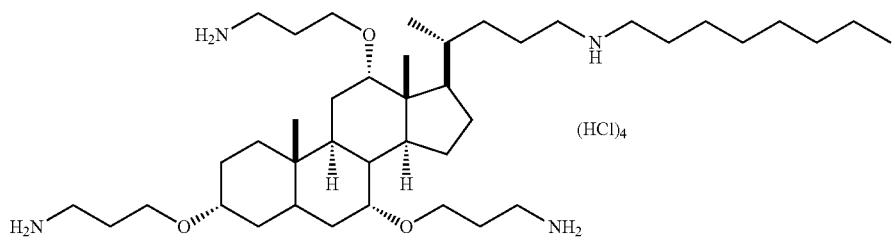

a compound of Formula (III):

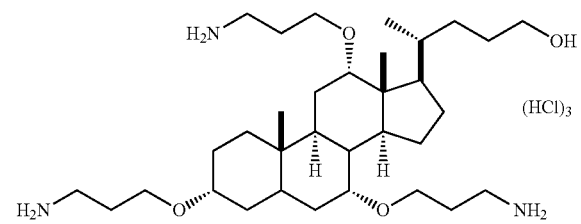

In some embodiments, the cationic steroidal compound is a compound of Formula (II):

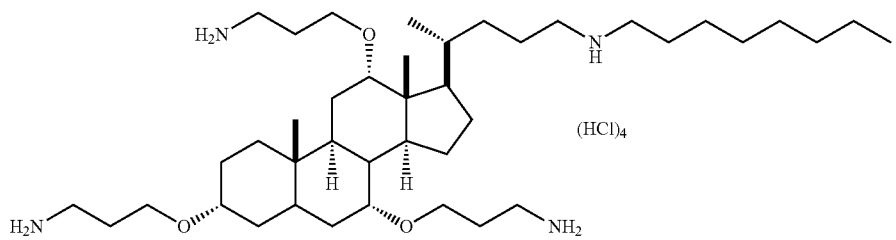

In some embodiments, the cationic steroidal compound has a molecular weight of from about 500 to about 1000. In some embodiments, the cationic steroidal compound has a molecular weight of from about 650 to about 850.

In some embodiments, the cationic steroidal compound is present at a concentration of from about 0.01% to about 0.1%, by weight, of the composition. In some embodiments, the cationic steroidal compound is present at a concentration of about 0.05%, by weight, of the composition.

In some embodiments, the quaternary ammonium compound is selected from: benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride and domiphen bromide. In some embodiments, the quaternary ammonium compound comprises cetylpyridinium chloride.

Quaternary ammonium compounds are a group of ammonium salts in which organic radicals have been substituted for all four hydrogens of the original ammonium cation. They have a central nitrogen atom which is joined to four organic radicals and one acid radical. Examples of quaternary ammonium compounds suitable for use in the instant invention further include other benzalkonium or benzethonium halides, including, but not limited to, benzalkonium or benzethonium bromide or fluoride, cetyl p alkylamidopropalkonium chloride, behenalkonium chloride, behentrimonium methosulphate, behenamidopropylethyldimonium ethosulphate, stearalkonium chloride, olealkonium chloride, cetrimonium chloride, dequalinium chloride, N-myristyl-N-methyl-morpholinium methyl sulfate, poly[N-[3-(dimethylammonio) propyl]-N'-[3-(ethyleneoxyethelenedimethylammo-inio) propyl]urea dichloride], alpha-4-[1-tris(2-hydroxyethyl) ammonium chloride-2-butenyl]-omega-tris(2-hydroxyethyl) ammonium chloride, poly[oxyethylene(dimethyliminio) ethylene(dimethyliminio)-ethylene dichloride].

In some embodiments, the quaternary ammonium compound is present at a concentration of from about 0.01% to about 0.1%, by weight, of the composition. In some embodiments, the quaternary ammonium compound is present at a concentration of about 0.05%, by weight, of the composition.

In some embodiments, the cationic steroidal compound and the quaternary ammonium compound are present in a 1:1 ratio, based on their respective concentrations, by weight, in the composition.

Some embodiments of the present invention further comprise a fluoride ion source, wherein the fluoride ion source is selected from stannous fluoride, sodium fluoride, potassium fluoride, sodium monofluorophosphate, sodium fluorosilicate, ammonium fluorosilicate, amine fluoride, ammonium fluoride, and a combination of two or more thereof. In some embodiments, the fluoride ion source comprises sodium fluoride.

Other embodiments provide a method of treating a disease or condition of the oral cavity comprising administering a composition according to any of the foregoing claims to the oral cavity of a subject in need thereof. In some embodiments, the disease or condition of the oral cavity is an inflammatory disease or condition. In some embodiments, the disease or condition is selected from gingivitis, periodontitis, and caries.

In some embodiments, the present invention provides methods of treating an inflammatory condition of the oral cavity, comprising administering a composition comprising a cationic steroidal compound to the oral cavity of a subject in need thereof.

Some embodiments provide a method of treating oral malodor comprising administering an effective amount of a composition of the present invention to the oral cavity of a subject in need thereof. In some embodiments, the compositions of the present invention reduce volatile sulfur compounds (VSC) generated from odor producing salivary bacteria.

The present inventors have discovered that a combination of a cationic steroidal compound (e.g., a ceragenin) and a quaternary ammonium compound (e.g. cetylpyridinium chloride) provides an unexpectedly enhanced antimicrobial activity As used herein the term "a ceraginin" includes combinations of ceragenins and "a quaternary ammonium compound" includes combinations of quaternary ammonium compounds.

Ceragenins are cationic steroid antibiotics (CSAs). They can be synthetically produced and are small molecule chemical compounds consisting of a sterol backbone with amino acids and other chemical groups attached to them. These compounds have a net positive charge that is electrostatically attracted to the negatively charged cell membranes of certain viruses, fungi and bacteria. CSAs have a high binding affinity for such membranes and are able to rapidly disrupt the target membranes leading to rapid cell death.

The cationic properties of ceragenins mimic the cationic charge of peptides. Ceraginins contemplated to be useful in the present invention are disclosed in U.S. Pat. No. 6,767,904. In one embodiment the ceraginin is a compound of Formula (II):

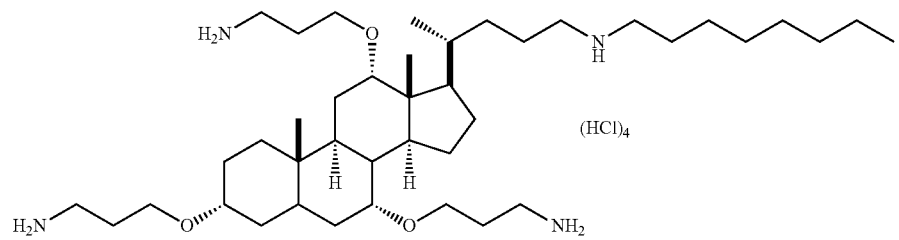

The biological activity of the ceragenin and quaternary ammonium compounds can be determined by standard methods known to those of skill in the art, such as the "minimum inhibitory concentration (MIC)" assay, whereby the lowest concentration at which no change in optical density (OD) is observed for a given period of time is recorded as MIC. When the compound alone is tested against a control that lacks the compound, the antimicrobial effect of the compound alone is determined.

Alternatively, "fractional inhibitory concentration (FIC)" is also useful for determination of synergy between the compounds. The use of the terms, "synergistic" and "synergy," are used in the present invention to mean an antibacterial effect created from the application of two or more compounds to produce an antibacterial effect that is greater than the sum of the antibacterial effects produced by the application of the individual compounds. The FIC procedure permits determination of synergistic effects of a combination of the compounds. FICs can be performed by checkerboard titrations of one compound in one dimension of a microtiter plate, and of the other compound in the other dimension, for example. The FIC is calculated by looking at the impact of one compound on the MIC of the other and vice versa. An FIC of one indicates that the influence of the compounds is additive and an FIC of less than one indicates synergy. In some embodiments, an FIC of less than 0.7 indicates synergy between the compounds being evaluated.

As used herein, FIC can be determined as follows:
FIC=A+B where A=(MIC of combination X+Y/(MIC of X alone)
B=(MIC of combination X+Y/(MIC of Y alone)

The combination of antimicrobial compounds of the present invention is effective against a wide variety of microorganisms such as oral bacteria. Examples of such bacteria include, but are not necessarily limited to, *Actinomyces viscosus, Streptococcus mutans, Porphyromonas gingivalis, Fusobacterium nucleatum*, and the like.

In some embodiments, the compositions of the present invention are able to provide the antimicrobial effect after about 30 seconds. This ability is particularly advantageous for the embodiments of the present invention which are in the form of a mouthwash, as 30 seconds corresponds to the ordinary duration of use for a mouthwash.

In some embodiments, the compositions comprise a buffering agent, e.g., sodium phosphate buffer (e.g., sodium phosphate monobasic and disodium phospate).

In some embodiments, the compositions comprise a humectant. Humectants useful herein include polyhydric alcohols such as glycerin, sorbitol, xylitol or low molecular weight PEGs, alkylene glycol such as polyethylene glycol or propylene glycol. In various embodiments, humectants are operable to prevent hardening of paste or gel compositions upon exposure to air. In various embodiments humectants also function as sweeteners. In some embodiments, the humectant is present in the amount of about 1 to about 40% each by weight. In some embodiments, the humectant is sorbitol. In some embodiments sorbitol present at a concentration of from about 5 to about 25%, by weight. In some embodiments sorbitol present at a concentration of from about 5 to about 15%, by weight. In some embodiments, the sorbitol is present at a concentration of about 10%, by weight. Reference to sorbitol herein refers to the material typically as available commercially in 70% aqueous solutions. In some embodiments, the total humectant concentration is from about 1 to about 60%, by weight. In some embodiments, the humectant is glycerin. In some embodiments, glycerin is present at a concentration of from about 5 to about 15%, by weight. In some embodiments, glycerin present is at a concentration of about 7.5%, by weight. In some embodiments, the humectant is propylene glycol. In some embodiments, propylene glycol is present at a concentration of about 5 to about 15%, by weight. In some embodiments, propylene glycol is present at a concentration of about 7%, by weight.

In some embodiments, the compositions comprise a cellulosic polymer such as hydroxyalkyl methyl celluloses (such as hydroxypropyl methyl cellulose, hydroxybutyl methyl cellulose, hydroxyethyl methyl cellulose, hydroxymethyl methyl cellulose and hydroxyethylpropyl methyl cellulose); carboxyalkyl methylcelluloses (such as carboxypropyl methyl cellulose, carboxybutyl methyl cellulose, carboxyethyl methyl cellulose, carboxymethyl methyl cellulose and carboxyethylpropyl methyl cellulose); hydroxyalkyl celluloses (such as hydroxypropyl cellulose, hydroxybutyl cellulose, hydroxyethyl cellulose, hydroxymethyl cellulose and hydroxyethylpropyl cellulose); alkyl celluloses (such as propyl cellulose, butyl cellulose, ethyl cellulose, methyl cellulose); carboxyalkyl celluloses (such as carboxypropyl cellulose, carboxybutyl cellulose, carboxyethyl cellulose, carboxymethyl cellulose and carboxyethylpropyl cellulose), and combinations thereof In some embodiments, the cellulosic polymer comprises carboxymethyl cellulose.

In some embodiments, the compositions comprise a gum polymer such as carrageenan gum, xanthan gum, and combinations thereof In some embodiments, the gum polymer comprises xanthan gum.

Some embodiments comprise a polyacrylate polymer or co-polymer such as a carbomer. In some embodiments, the polyacrylate polymer or co-polymer is selected from homo- and copolymers of acrylic acid crosslinked with a polyalkenyl polyether. Synthetic high molecular weight polymers of acrylic acid known as carbomer may be homopolymers of acrylic acid, crosslinked with an allyl ether pentaerythritol, allyl ether of sucrose or allyl ether of propylene. Carbomer has a USP classification of "carbomer homopolymer Type A". Carbomers have the ability to adsorb, retain water and swell to many times their original volume. Carbomers codes (910, 934, 940, 941, 971, 974 and 934P) are an indication of molecular weight and the specific components of the polymer. Carbomers are commercially available, under the trade name Carbopol® from Lubrizol and other companies.

Some embodiments provide a composition obtained or obtainable by combining the ingredients as set forth in any of the embodiments described herein.

In some embodiments, the composition is in the form selected from a mouthwash, mouthrinse, mousse, foam, mouth spray, lozenge, tablet, dental implement, and a pet care product. In some embodiments, the composition is a mouthwash or mouthrinse.

Some embodiments of the present invention provide aqueous compositions comprising the following ingredients by weight:

| Ingredient | Concentration Range % wt/wt |
| --- | --- |
| Water | 50-90 |
| Humectants | 1-25 |
| Surfactant | 0.01-10 |
| Preservative | 0.01-1 |
| Flavor | 0.01-1 |
| Cellulosic polymer | 0.01-0.5 |
| Gum polymer | 0.01-0.5 |
| Polyacrylate polymer or co-polymer | 0.01-0.5 |
| Sodium fluoride | 0-0.05 |
| Ethyl alcohol | 0-8 |
| Sweetener | 0.01-0.5 |
| Cetylpyridinium chloride | 0.01-1 |
| Compound of Formula | 0.01-1 |

Some embodiments provide a method of treating halitosis comprising administering any embodiment of the present invention to the oral cavity of a subject in need thereof.

Some embodiments comprise colorants. Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl)indanedione, FD&C Yellow No. 5 (sodium salt of 4-psulfophenylazo-1-p-sul-fophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-.DELTA.-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

Flavor agents may also be included in some embodiments of the present invention. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavor agents can be used individually or in admixture. Commonly used flavors include mints such as peppermint, artificial vanilla, cinnamon derivatives, and various fruit flavors, whether employed individually or in admixture. Generally, any flavoring or food additive, such as those described in Chemicals Used in Food Processing, publication 1274 by the National Academy of Sciences, pages 63-258, may be used. Typically, flavorants if included are present at 0.01-1%, by weight. In some embodiments, flavoring may be present in about 0.2%, by weight.

Sweeteners include both natural and artificial sweeteners. Suitable sweetener include water soluble sweetening agents such as monosaccharides, disaccharides and polysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). In general, the effective amount of sweetener is utilized to provide the level of sweetness desired for a particular composition, will vary with the sweetener selected. This amount will normally be about 0.001% to about 5% by weight of the composition. In some embodiments, the sweetener is sodium saccharin and present at about 0.01% by weight of the composition.

Optional breath freshening agents may be provided. Any orally acceptable breath freshening agent can be used, including without limitation zinc salts such as zinc gluconate, zinc citrate and zinc chlorite, alpha-ionone and mixtures thereof. One or more breath freshening agents are optionally present in a breath freshening effective total amount.

Optionally, the composition may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J.

In some embodiments, tartar control agent is present at a concentration of from about 0.01 to 10%, by weight. In some embodiments, the tartar control agent is present at a concentration of about 1%, by weight. In some embodiments, the tartar control agent also acts as a buffer. For example, in a phosphate buffer system, sodium phosphate monobasic is present at a concentration of from about 0.01 to about 5%, by weight, and disodium phosphate is present at a concentration of from about 0.01 to about 5%, by weight, the precise ratio depending upon the other excipients in the formulation and the desired pH.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof Also optional, saliva stimulating agent, useful for example in amelioration of dry mouth may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof.

In some embodiments, the methods comprise the step of rinsing the oral cavity with a composition as described herein. In some embodiments, 5 ml or more of the composition is gargled. In some embodiments, 10 ml or more is used. In some embodiments, 10-50 ml is used. In some embodiments, 15-25 ml or more is used. In some embodiments, 15 ml or more is used. In some embodiments, the individual gargles with the composition multiple times per day. In some embodiments, the individual gargles with the composition on multiple days. In some embodiments, the individual gargles with the composition every 4 to 6 hours up to 6 times per day.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Table 1 (below) describes the formulation for two exemplary compositions of the present invention (Composition I and Composition II).

TABLE 1

| Ingredient | Composition I Wt. % | Composition II Wt. % |
|---|---|---|
| Sucralose | 0.02 | 0.02 |
| Sodium Fluoride | 0.05 | 0.05 |
| Sodium Benzoate | 0.11 | 0.11 |
| Glycerin | 7.5 | 7.5 |
| Sorbitol | 5.5 | 5.5 |
| Propylene Glycol | 5 | 5 |
| Pluronic F127 | 0.15 | 0.15 |
| Ethyl Alcohol | — | 6 |
| Water | 81.57 | 75.57 |
| Cetylpyridinium chloride | 0.05 | 0.05 |
| Compound of Formula (II) | 0.05 | 0.05 |
| Total | 100 | 100 |

Example 2

Exemplary Method of Preparation

Some embodiments of the present invention can be prepared according to the following procedure. A pre-mix is prepared by adding propylene glycol to a container and adding menthol thereto. The combination is mixed until the menthol is dispersed. Flavor is added and mixed for about 3 minutes. Water is then added to the main mixer and the mixer is turned on. Pluronic is then added until it is sufficiently dispersed. Saccharin, potassium sorbate and a compound of Formula (II) are then added to the main mixer and mixed for about 3 minutes. Citric acid is added to the main mixer and mixed for about 5 minutes. Glycerin is added to the main mixer. Sorbitol is added to the main mixer and the mixed for about 5 minutes. The pre-mix is then added to the main mixer and mixed for about 15 minutes.

Example 3

To evaluate minimum inhibitory concentrations (MICs), the concentration of the twenty four hour culture in log phase is adjusted by diluting in tryptic soy broth (TSB) so that an optical density of 0.2 at 610nm is obtained. The bacterial culture is then ready to be used for testing.

Three solutions are prepared: (1) 1% CPC solution in ethanol; (2) 1% solution of the Compound of Formula (II) in water; and (3) 0.5% of a Compound of Formula (II) +0.5% CPC. The solutions are diluted 1:9 in TSB. They are added to a 96-well plate and a serial dilution (2-fold) is made across the plate. The bacterial inoculum at 0.2 OD, 1000, is added to every well. The plate is incubated overnight and read on a plate reader the following day.

TABLE 2

| Active | MIC (ppm) |
|---|---|
| Negative Control | >250 |
| Compound of Formula (II) | 0.49 |
| CPC | 0.98 |
| Compound of Formula (II) + CPC | <0.12 |

0.5% CSA-13 + 0.5% CPC is <0.4 = synergistic

Example 4

Water is used as a negative control. 0.04 mL of each sample is added into a GC headspace vial with each sample being tested in duplicate. A saliva inoculum is prepared using 65% whole saliva collected after lunch, 30% deionized water, and 5% of FTG media. Three milliliters of the saliva mixture is added to the vials containing the samples. The vials containing the saliva mixture and samples are capped.

The capped vials are incubated overnight at 37° C. in a water bath with shaking Gas chromatography (GC) is utilized to determine the amount of reduction of volatile sulfur compounds (VSC) as compared with the negative control.

The data described in Table 3 (below) demonstrates that compositions of the present invention are effective in reducing volatile sulfur compounds, and would therefore likely be effective in treating oral malodor.

TABLE 3

| Formulation | Reduction in VSC |
|---|---|
| Negative Control | 13.1 |
| 0.05% Compound of Formula (II) | 97 |

Example 5

In this assay, two fluorescent dyes are used to give a rapid measure of bacteria viability.

A sample from a mixed species bacterial chemostat culture, OD –0.6 is transferred to sterile 1.5 mL microcentrifuge tubes and centrifuged for 10 min at 12,000×g to pellet the bacteria. Bacteria are then resuspended in 100 ut, of sterile phosphate buffered saline (PBS). Samples are treated with 100 ut, (high dose) or 20 ut, (low dose) of mouthwash or control solution. Killing is stopped after 30 seconds, as indicated by the addition of 1.35 mL of D/E Neutralization Buffer (Invitrogen). Samples are centrifuged for 10 min at 12,000×g to pellet bacteria and pellets are resuspended in 500 ut, of sterile PBS to wash, then centrifuged again. Finally samples are suspended in 150 ut, of sterile PBS and 50 ut, aliquots are transferred to each of three wells of sterile 96-well plates, which are subjected to bacteria staining using Invitrogen BacLight Live/Dead bacterial viability kit. 50 ut, of 2× solution containing two dyes (SYTO9 dye [green] and propidium iodide [red]) are added to samples in the 96-well plates. Plates are incubated for 15 min at room temperature, protected from light and subjected to fluorescence reading at excitation wavelength 485 nm and emission wavelength 535 and 635 nm. Results are presented as a percentage of cells that are viable relative to a control sample treated with PBS.

Table 4 (below) describes data demonstrating that the compositions of the present invention provide a synergistic antimicrobial effect after 30 seconds of use.

TABLE 4

| Formulation | Log Reduction at 30 Seconds |
| --- | --- |
| 0.05% CPC | 3.93 |
| 0.05% Compound of Formula (II) | 0.38 |
| 0.05% Compound of Fomula (II) + 0.05% CPC | 7.52 |

Example 6

The anti-inflammatory activity of a compound of Formula (II) is studied against six human inflammatory cytokines, PGE2, IL-1B, IL-6, IL-8, TNF-a, and GM-CSF in separate sets of experiments; first against PGE2, then against the five other cytokines Human monocyte U937 cells are differentiated to macrophages and then generation of cytokines is induced by stimulating the cells using heat killed *P. gingivalis* (HKPG, 1×108 cells). Different types of inflammatory cytokines are generated by U973 cells and released into the supernatant.

A compound of Formula (II) displays higher anti-inflammatory efficacy against three cytokines, IL-1β, IL-6, and TNF-a. Specifically, at a concentration of 0.1 ppm, a compound of Formula (II) reduces 21% of IL-10, 60% of IL-6 and 80% of TNF-a.

The invention claimed is:

1. An aqueous oral care composition comprising:
   an aqueous carrier;
   a cationic steroidal compound of Formula (I):

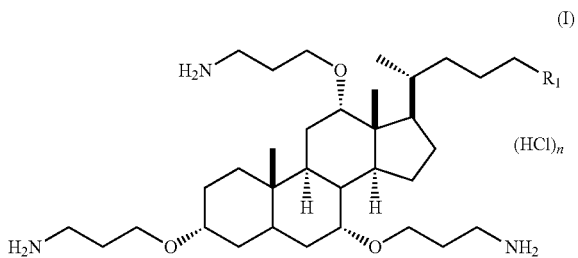

(I)

where,
   $R_1$ is selected from —OH and NH—$R_2$,
   $R_2$ is $C_2$-$C_{14}$ alkyl, $C_2$-$C_{14}$ alkenyl or $C_2$-$C_{14}$ akynyl, and
   n is 3 or 4; and
a quaternary ammonium compound, wherein the cationic steroidal compound is present at a concentration of from about 0.01% to about 0.1% by weight, of the composition.

2. The composition of claim 1, wherein the composition is a mouthwash.

3. The composition of claim 1, wherein the compound of Formula (I) is selected from a compound of Formula (II):

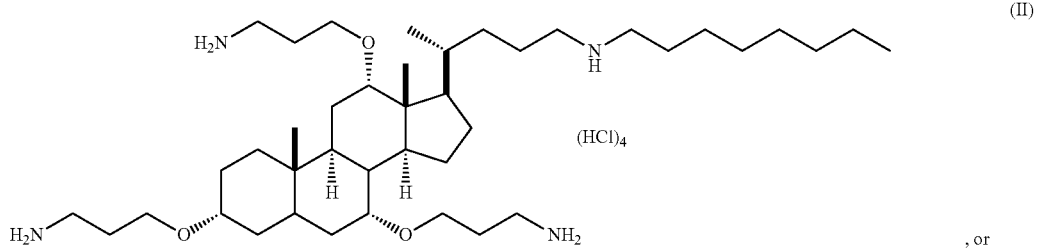

(II)

, or a compound of Formula (III):

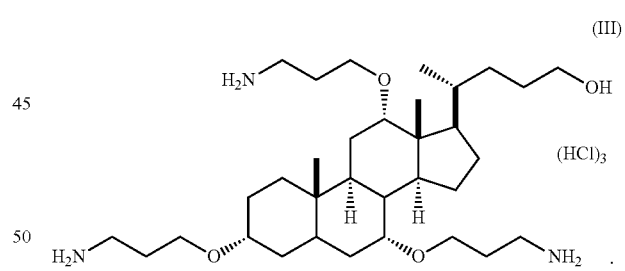

(III)

4. The composition of claim 1, wherein the cationic steroidal compound is a compound of Formula (II):

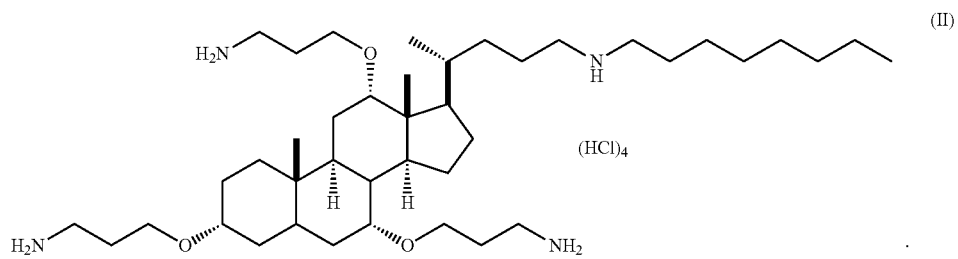

(II)

5. The composition of claim 1, wherein the quaternary ammonium compound is selected from the group consisting of benzalkonium chloride, benzethonium chloride, methylbenzethonium chloride, cetalkonium chloride, cetylpyridinium chloride, cetrimonium, cetrimide, dofanium chloride, tetraethylammonium bromide, didecyldimethylammonium chloride, and domiphen bromide.

6. The composition of claim 1, wherein the quaternary ammonium compound comprises cetylpyridinium chloride.

7. The composition of claim 1, wherein the quaternary ammonium compound is present at a concentration of from about 0.01% to about 0.1%, by weight, of the composition.

8. The composition of claim 1, wherein the cationic steroidal compound and the quaternary ammonium compound are present in a 1:1 ratio, based on their respective concentrations, by weight, in the composition.

9. The composition of claim 1, wherein the cationic steroidal compound is present at a concentration of about 0.05%, by weight, of the composition.

10. The composition of claim 1, wherein the quaternary ammonium compound is present at a concentration of about 0.05%, by weight, of the composition.

11. The composition of claim 1, further comprising a fluoride ion source; wherein the fluoride ion source is selected from stannous fluoride, sodium fluoride, potassium fluoride, sodium monofluorophosphate, sodium fluorosilicate, ammonium fluorosilicate, amine fluoride, ammonium fluoride, and a combination of two or more thereof.

12. The composition of claim 11, wherein the fluoride ion source comprises sodium fluoride.

13. A method of treating the oral cavity comprising administering a composition according to claim 1 to the oral cavity of a subject in need thereof.

* * * * *